United States Patent [19]
Kolff

[11] Patent Number: 4,902,291
[45] Date of Patent: Feb. 20, 1990

[54] COLLAPSIBLE ARTIFICIAL VENTRICLE AND PUMPING SHELL

[75] Inventor: Willem J. Kolff, Salt Lake City, Utah

[73] Assignee: University of Utah Research Foundation, Salt Lake City, Utah

[21] Appl. No.: 286,620

[22] Filed: Jan. 31, 1989

[51] Int. Cl.$^4$ .............................................. A61F 2/22
[52] U.S. Cl. ........................................... 623/3; 600/16
[58] Field of Search ........................ 623/3; 600/16, 17

[56] References Cited

U.S. PATENT DOCUMENTS

| | | | |
|---|---|---|---|
| 4,570,903 | 6/1988 | Cheng | 623/3 |
| 4,573,997 | 3/1986 | Wisman et al. | 623/3 |
| 4,578,077 | 3/1986 | Joh | 623/3 |

Primary Examiner—Richard J. Apley
Assistant Examiner—Stephanie L. Iantarno
Attorney, Agent, or Firm—Thorpe, North & Western

[57] ABSTRACT

An artificial ventricle for use as part of a total artificial heart for implantation within a living being as part of its circulatory system. The ventricle includes a soft and flexible blood pumping sac which can be collapsed to the substantially flattened, squeezed or rolled-up structure of much reduced size. The sac includes inlet and outlet ports to permit the flow of blood therethrough and is contained within a semi-rigid and removable enclosure which provides pumping means for driving blood flow through the ventricle. The semi-rigid shell includes open and closed configurations to allow emplacement of the shell around an attached ventricle already sutured in place as part of the circulatory system. Removal of the rigid shell is likewise feasible without disturbing the attached ventricle.

19 Claims, 3 Drawing Sheets

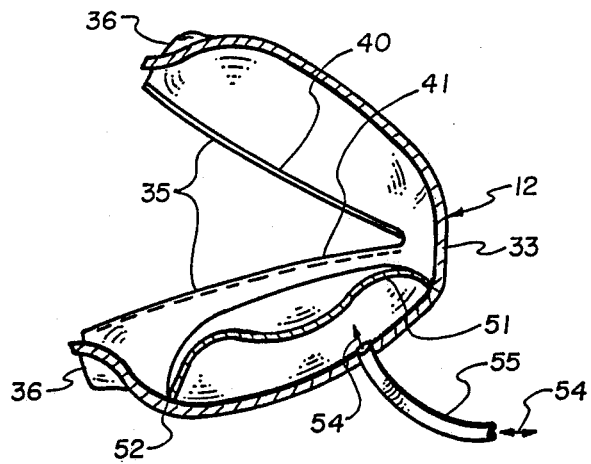
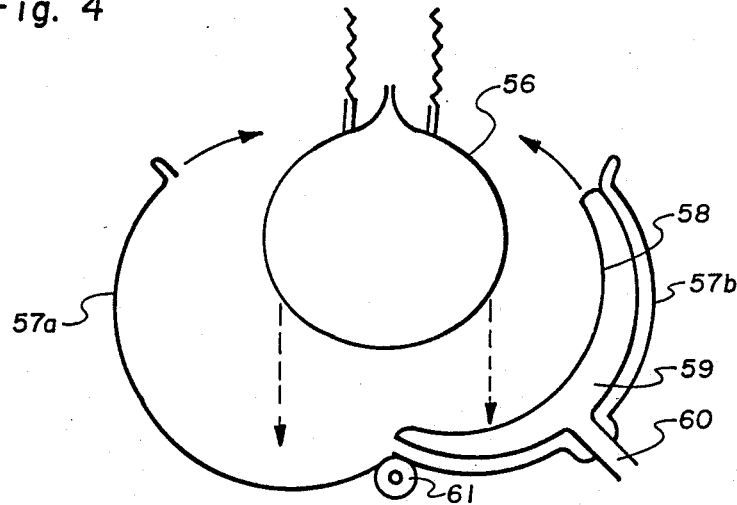
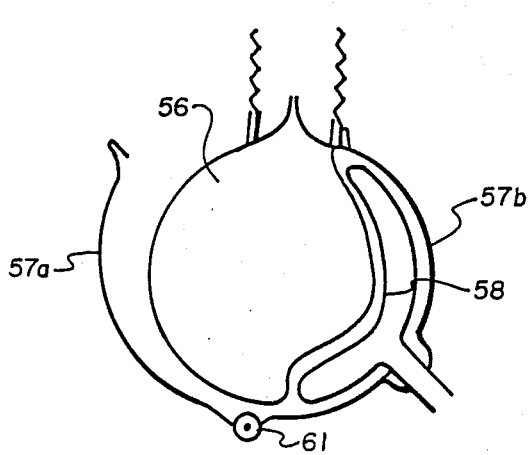
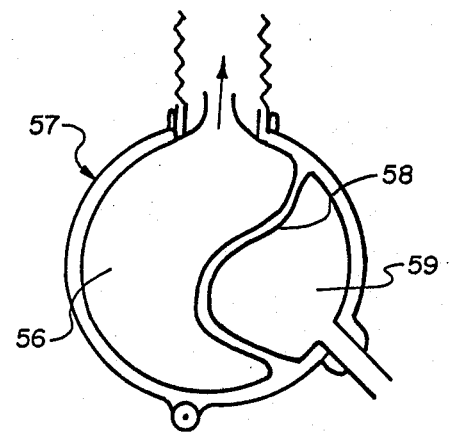
Fig. 4
Fig. 5
Fig. 6
Fig. 7

COLLAPSIBLE ARTIFICIAL VENTRICLE AND PUMPING SHELL

BACKGROUND OF THE INVENTION

1. Field of Invention:

The present invention relates to artificial ventricles for use as part of a total artificial heart for implantation within a living being as part of its circulatory system. More specifically the present invention relates to an artificial ventricle which can be easily positioned and surgically implanted within the patient.

2. Prior Art:

The successful advent of the total artificial heart has offered new options for extending life of patients who are awaiting heart transplants or to provide a permanent replacement if a donor heart is not available. The need for such artificial hearts is critical in view of the limited availability of donor hearts (no more than 2,000 donor hearts are available per year) as compared to the patient demand for such transplants exceeding 33,000 per year in the United States alone. Whereas terminal patients who might otherwise have little hope for survival because of the great shortage of donor hearts have little hope except as may be provided by total artificial heart systems, greatly increased attention has been given to improving such devices to overcome the myriad of technical hurdles associated with mechanically replicating the structure and performance of the natural human heart. One of the greatest challenges in connection with improving this field of technology is reduction in size of the total artificial heart and its supporting component structure to adapt to the limited physical space within the chest cavity and for its implantation. The implantation procedure requires physical space to suture the artificial atrium, aorta and pulmonary artery to their natural counterparts. Failure to achieve proper suturing of junctions with the soft tissue of the circulatory system would be a major cause of hemorrhage (bleeding), breaking of suture lines causing dehiscence and thrombogenesis.

Unfortunately, a mere reduction in size of the artificial ventricle is not a solution to the problem. Minimum stroke volumes are required to maintain adequate blood flow to support life systems of the human body. Accordingly, the artificial heart must have sufficient cavity volume to enable adequate stroke volume for pumping blood through the circulatory system. To date, man's technology has been unable to duplicate the compactness, the softness and pliability and efficiency of the natural human heart with total artificial heart systems.

The Jarvik-7 total artificial heart is characteristic of prior art devices within this general field of technology. Specifically, their ventricles are of singular construction and include a rigid casement which includes a blood flow compartment and pumping compartment. These compartments are separated by one or more diaphragms which alternately extend and contract in response to a fluid drive system which alternates between positive and negative pressure within the pumping compartment. Because of the difficulty of suturing the artificial heart and attached valve structure within the chest cavity, quick-connect couplers were developed to be sutured to the atrium, aorta and pulmonary arteries before attachment of the artificial ventricles. This provided some room for the surgeon to work within the limited chest cavity space. Once the quick connect couplers were sutured to the soft tissue of the circulatory system, the artificial ventricles would then be quick coupled at their valve openings or with their artificial atria, aorta and pulmonary artery to their natural counterpart within the chest cavity.

Unfortunately, special equipment is required for testing the suture lines. After connection of the rigid ventricle, these suture lines are difficult to reach. The quick connects enhance the risk of thrombogenesis at the quick coupling sites and even more so if the valves are incorporated in them.

Because of these and other limitations, widespread use of the total artificial heart is still limited. What is needed is artificial ventricles which are more easily implanted and which do not impose the severe spacial restraints which result from the rigid artificial hearts of the prior art.

OBJECTS AND SUMMARY OF THE INVENTION

It is therefore an object of the present invention to provide an artificial ventricle which ca be surgically implanted without the need of quick connects and which enables evaluation of complete suturing and other operational aspects of the ventricle prior to functional operation of the artificial heart.

It is a further object of the present invention to provide artificial ventricles which can be compressed or reduced in size to much smaller volume to facilitate working room for the surgeon during suturing and implantation.

It is a still further object of the present invention to separate the soft ventricle structure from the more rigid pumping structure of a total artificial heart to simplify implantation procedures.

These and other objects are realized in an artificial ventricle which comprises a soft and flexible blood pumping sac which incorporates an extended or diastolic configuration and a contracted or systolic configuration provided by wall structure having sufficient size to develop adequate stroke volume for sustaining life within the living being. The blood sac is characterized by sufficient flexibility to collapse to a substantially flattened or rolled up structure of reduced size to facilitate surgical implantation within the restricted space of the chest cavity. The ventricle includes an inlet port positioned within the wall structure and including means for attachment to the atrium or other soft tissue of the circulatory system, along with means for receiving a one way valve to control blood flow. An outlet port is also positioned within the wall structure and includes means for attachment to the aorta, pulmonary artery or other soft tissue of the circulatory system to form a continuous flowline therewith. A one way valve is also provided with respect to the outflow (flow) port to enable unidirectional blood flow in response to pumping activity of the ventricle. The present invention also includes a semi-rigid shell which is structurally separate from the blood pumping sac and includes closure means for developing closed and open configurations which respectively permit insertion around and removal from the blood pumping sac in the chest cavity. The closure means and shell provide a closed shell configuration which is slightly larger in shape and size at its interior surface than the extended configuration of the wall structure of the blood pumping sac and is structured to totally close the sac in a confining manner. This shell includes an opening for the inlet and outlet ports and sealing means to provide a circumferential seal at junctures of the shell with the respective inlet and outlet ports. The closure means of the shell also provides an open configuration which enables insertion of the contracted sac through a shell opening or removal of the shell from around the sac without affecting attachment of the sac as part of the circulatory system. Pumping means are coupled through the rigid shell to enable alternating extension and collapse of the blood pumping sac in recurring pumping manner when the shell is in the closed configuration to thereby allow inflow and expulsion of blood from the blood sac.

Other objects and features of the present invention will be apparent to those skilled in the art based on the following description, taken in combination with the accompanying drawings.

DESCRIPTION OF THE DRAWINGS

FIG. 4 is a cross section of the shell structure of FIG. 1, taken along the lines 4—4.

FIG. 5 is a graphic representation representing enclosure of the blood sac within the rigid shell.

FIG. 6 graphically illustrates a sequential step in the attachment of the rigid shell around the blood sac.

FIG. 7 illustrates the closed position of the shell around the blood sac, with a pumping compartment of the shell somewhat extended in response to pumping fluid pressure.

DETAILED DESCRIPTION OF THE INVENTION

Figure 1:
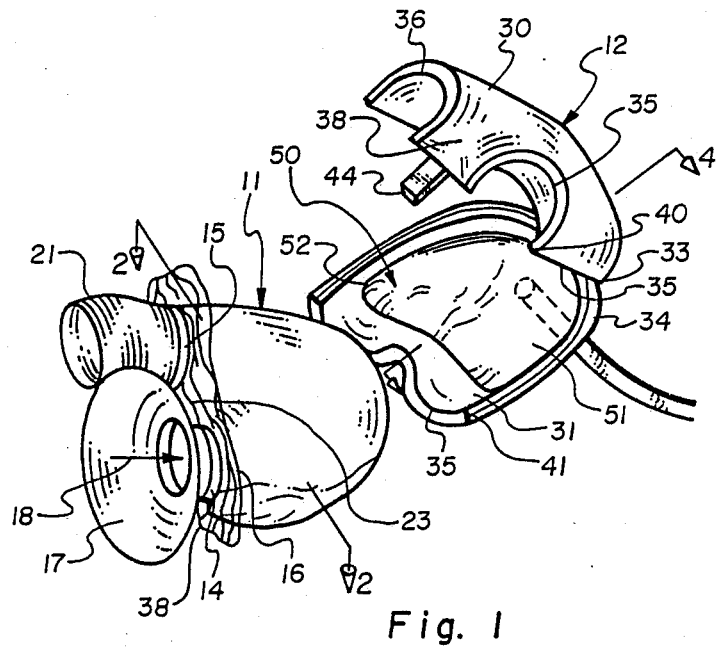
FIG. 1 shows a perspective view of the two components of the present invention including a soft and flexible artificial ventricle at the left and a semi-rigid shell structure at the right which encloses around the ventricle.
Figure 2:
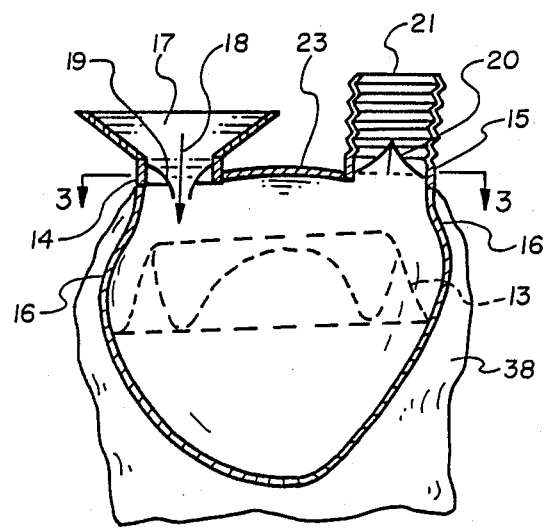
FIG. 2 is a cross section of the ventricle shown in FIG. 1, taken along the lines 2—2.

Referring now to the drawings:

FIG. 1 shows a generic form of the subject invention which includes two basic components. The first component is a blood pumping sac 11 and a second component is a semi-rigid shell 12 which is configured to fit snugly around the blood sac 11 when it is in its fully extended configuration as shown in FIG. 1. Specifically, the blood sac 11 includes two positions, one for the diastolic or extended configuration when the blood sac is filled with blood during a pumping cycle, and a second contracted configuration representing the systolic phase wherein the contained blood has been expelled by reason of the reduced volume of the blood sac. It will be apparent that the blood sac must have wall structure of sufficient size in containment to develop adequate stroke volume for sustaining life within the living being depending upon blood circulation by reason of this device. In addition, the blood sac needs to have sufficient flexibility to collapse to a substantially flattened or rolled up soft structure of reduced size as shown by the phantom lines 13 of FIG. 2. This much reduced size permits ease of surgical implantation within the restricted space of the chest cavity.

This blood sac 11 provides a fully enclosed cavity except for an inlet port 14 and outlet port 15. The inlet port is positioned within the wall structure 16 and includes an atrial cuff 17 or other means for attachment to the atrium or other soft tissue of the circulatory system to form a continuous flowline 18 therewith. The inlet port 14 would also include some form of one way valve 19 for insuring proper direction 18 of blood flow into the ventricle.

The outlet port 15 likewise includes a one way valve 20 or means for receiving such a valve to control unidirectional blood flow. The outlet port is positioned within the wall structure 16 of the blood sac and includes a graft 21 or other means for attachment to the aorta, pulmonary artery or other soft tissue within the circulatory system to close the required blood flow line.

The preferred construction of the blood sac 11 is a thin walled structure of silicon or Silastic (trademark registered to Dow Corning) or polyurethane material. This polymer should be soft and flexible to enable its collapse to a flat or rolled configuration 13 so that the blood sac takes up minimal space within the chest cavity during implantation. The present inventor has discovered that current silicon materials provide surprising and unexpected adaptability for use as an artificial ventricle, despite lack of application in this area in the last ten years. Silicon does have the benefit of being nonbiodegradable and the inventor has discovered certain silicon materials that have sufficient strength to provide the survivability required for use as part of an artificial heart. This new silicon material is identified under the tradename of Silastic HP-100 and has proven particularly suited for this application based on laboratory tests to date. Specifically, HP-100 Silastic pumping membrane made by injection molding has been tested in real time while it was protected against overdistension by a polyurethane membrane. Its life duration has already exceeded 20,000,000 cycles without sign of undue stress.

Similarly, artificial ventricles made of the new HP-100 Silastic, plus Silastic valves, have been tested in mock circulation systems by the inventor. These tests have included both functional tests as to operation characteristics, as well as for blood compatibility measurement in a thrombus-provoking blood bag. Here again, the results have been positive at both levels of evaluation.

Where one adopts the more favorable Silicone materials over prior art polyurethane construction, it is important that the methods of fabrication carefully incorporate the differences required for use of Silicone materials. For example, Silicone is much more distensible and accordingly requires greater care. Silicone is also thermosetting, whereas the polyurethane is thermoplastic. Consequently, differences in fabrication, as well as subsequent treatment and application require special attention to the environment as well as handling techniques. Furthermore, it is difficult to develop techniques for vacuum forming Silicones, as compared to this method being the preferred fabrication procedure for polyurethanes. It is particularly important to note that the newer form of HP-100 Silicone elastomer requires different handling than the older Silicones which were used to make artificial hearts in the 1960's and early seventies. A final observation with respect to use of the new Silastic materials is that design limitations must be observed with respect to the strength of the material. Specifically, Silastic is durable but not very strong. The material in its fabricated form must therefore be protected by the use of safety membranes or safety chambers in the airline, or by screens to limit the extension of a pumping membrane in the diastole phase. It is believed that the discovery that Silicone polymers such as the new HP-100 available through Dow Corning represents a major step forward in artificial ventricle technology and one of an unexpected nature based on past inadequacies well known to those skilled in the art for Silicone materials.

In contrast to the soft and flexible structure of the blood sac 11, the inlet and outlet ports are generally best constructed of semi-rigid materials and may be interconnected by a bridging structure 23. The purpose of this more rigid bridging structure 23 is to maintain the respective inlet and outlet ports in relatively fixed positions during surgical implantation and subsequent use. These fixed positions conform to the proper location of the cuff 17 and graph 21 with respect to the attached soft tissue.

It will be apparent to those skilled in the art that the soft and flexible blood sac 11 disclosed in the figures and by description herein is intended to be exemplary of the general concept of a collapsible or foldable soft ventricle which can be substantially reduced in size during surgical implantation, thereby giving greater working space to the physician as appropriate suturing occurs with respect to the soft tissue points of attachment. It is to be understood, therefore, that this prior description is not to be considered limiting, but that other forms, configurations and compositions may be utilized to adopt this general concept as part of a total artificial system.

The second component of the subject invention comprises the semi-rigid shell 12 which is structurally separable from the blood pumping sac 11 and as shown in FIG. 1. In this embodiment, the shell is disclosed with two shell components 30 and 31. Although these illustrated components comprise approximately half-sections of the shell structure, it will be apparent to those skilled in the art that differing dimensions could likewise be applied wherein one shell component was of a lesser size than the second. The primary feature of the shell is to enable emplacement around the blood pumping sac 11 or subsequent removal therefrom. Therefore, the essential element of the shell is some form of opening means which permits such removal or emplacement.

In the illustrated embodiment, the shell includes two shell components 30 and 31 which are joined at a hinge section 33 or other form of closure means disposed at the remote edge from the forward open position closest to the blood sac in FIG. 1 The connecting hinge element 33 couples the joining peripheries 34 and 35 to form a clam-shell configuration. This analogy appropriately corresponds to the capability of clamshells to open or close by means of a connecting hinge or muscle joining one edge of the two shelled component structure. Similarly in the present case, the clam-shell configuration of this invention is capable of opening to permit insertion of the blood sac 11 and of closing around the blood sac to form a confining shell structure to limit expansion and displacement of the blood sac in response to operation of a pumping means. Accordingly, it is important for the shell and hinge or other form of enclosure means to totally enclose the sac up to the stiff ring 23 and inserted inlet and outlet ports 14 and 15. The interior surface of the shell is to be slightly larger in shape and size than the extended configuration of the wall structure of the blood pumping sac. Obviously, in this condition, the blood pumping sac is filled with blood and occupies substantially the full volume of the closed shell.

The shell illustrated in the figures includes an opening section or sections 35 and 36 which are designed to seal tightly around the respective inlet 14 and outlet 15 ports and at the interconnecting bridge 23. These mating components provide a circumferential seal at their respective junctures to prevent fluid exchange between the shell and the chest cavity.

A skirt member 38 may be provided to extend over the bridge 23 to facilitate a frictional seal, which may likewise be enhanced with adhesives. This skirt member 38 is attached at the bridge 23 and ports 14 and 15 or may simply include opening for emplacement around the blood sac ports much like a poncho. It is geometrically configured to conform to the exterior geometry of the semi-rigid construction of the ports and interconnecting bridge structure. During implantation, it is folded up or rolled up around the neck (FIG. 1) and will be deployed downwards over the entire artificial heart (FIG. 2) only after the implantation is completed and the heart is closed. One purpose is to offer an acceptable surface, such as DACRON Velour (trademark), to the surrounding tissues which will provide it with a thin, smooth layer of pseudoendothelium. It will be apparent that many forms of sealing mechanisms can be adopted in a similar manner to accomplish the objectives required for this invention.

Figure 3:
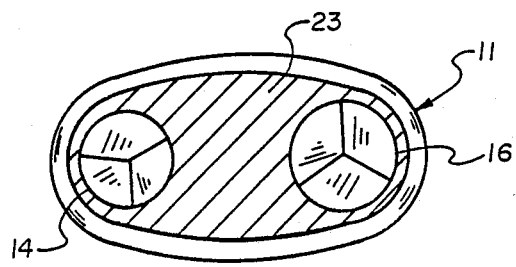
FIG. 3 is a cross section of interconnecting bridge structure and the inlet and outlet ports taken along the lines 3—3.

Likewise, specific sealing structure can be applied around the peripheral edges of the clamshell structure to insure a complete sealed juncture at peripheries 35 of the respective shell halves. FIGS. 1 and 3 illustrate the use of tongue and groove construction wherein interior channel 40 provides a sealing seat for a raised flange 41 in opposing orientation on the contacting periphery of the shell. The sealed configuration of the shell at its tongue and groove peripheries 40 and 41 and at the skirt member 38 can be secured by means of a latch member 44, by adhesives or numerous other methods of securing the closed configuration of the shell. The illustrated latch is coupled near the shell opening and may operate with respect to latching means (not shown) at an opposing side of the skirt member 38 on the second shell component.

The shell structure also incorporates a pumping mechanism 50 which is coupled through the rigid shell 12 to enable alternating extension and collapse of a blood pumping sac 11 in a recurring pumping manner when the shell is in the closed configuration. Such pumping action is characteristic for artificial ventricles and provides the required inflow and expulsion of blood from the blood sac. Specifically, this pumping means 50 includes a fluid drive sac 51 which is integrally formed or adhesively attached at an interior surface 52 of the shell. This drive sac 51 is structured of flexible material and has sufficient volume during expansion with the shell in the closed configuration to develop the desired stroke volume for the ventricle. FIG. 4 illustrates a partially extended configuration of the drive sac in response to air flow 54 through a fluid drive line 55 which is utilized to deliver fluid to extend and contract the drive sac during pumping action. Specific construction and support pumping mechanisms are well known within the art and need no further explanation with respect to the present invention. Such drive systems may include either air, hydraulic fluid or other pressure sensitive flow systems, depending on the particular application of the ventricle employed.

Utilization of the present invention is illustrated by the following example. Initially, the blood pumping sac 11 is compressed, rolled up or otherwise flattened to minimize its structural size (see hyphenated lines 13 in FIG. 2) and is positioned within the chest cavity with atrial cuff 17 in proximate location for suturing to the atrium and graft 21 and its location for attachment to the pulmonary artery or aorta. The much reduced size of the ventricle permits the surgeon greater freedom of movement to perform the suturing and to visually inspect the attached ventricle upon implantation. At this stage, the blood pumping sac 11 is continuous with the atrium and the aorta on the left side and a comparable ventricle is continuous with the atrium and pulmonary artery on the right side. In the preferred embodiment, inlet and outlet valves 19 and 20 are already incorporated as part of these flexible blood pumping sacs.

After the suture lines with the natural atria, the natural aorta or the natural pulmonary artery have been completed, any residual air can be easily expelled with a cannula inserted via the natural atrium. By utilizing blood sacs which are clear, any residual air can be easily detected and voided from the ventricle. The blood sac is then allowed to fill with blood and the natural atrium and aorta are then clamped off. The suture lines can then be put under pressure by compressing the ventricles to confirm that the suture lines are tight and the heart is properly prepared for operation. These procedures are greatly facilitated by the absence of a heart shell or container as provided in the prior art. This represents a major step forward in ease and safety for this difficult and critical stage of artificial heart implantation. This stage of the procedure is represented by blood pumping sac 56 shown in FIG. 5.

The firm shell 57 is then placed over each ventricle. This shell is represented by two components 57a and 57b which are initially opened widely to permit insertion over the blood sac 56 in its sutured condition. The shell includes a pumping membrane 58 which defines the pumping chamber 59 coupled to a drive line 60. The shell members 57a and 57b are then closed and a mechanism is provided to insure proper alignment of the device on the left side between the atrium and the aorta, and on the right side between the atrium and the pulmonary artery. As previously mentioned, the interconnecting bridge shown in FIG. 3 provides part of this alignment positioning function. FIG. 6 illustrates the inserted position of the blood pumping sac 56 within the shell 57, with the pumping membrane 58 slightly displaced. Hinge means 61 is illustrated at the base of the respective shell members 57a and 57b to suggest the location of flexibility permitting opening and closing of the shell structure.

FIG. 7 illustrates the fully closed and sealed condition of the shell 57 about the blood pumping sac 56. The pumping membrane 58 is approaching its half full position in FIG. 7 and can be extended completely, almost reaching the other side 57 upon inflation of the pumping cavity or air sac 59. It will be apparent that a pusher plate or other mechanical device could be used in place of the air sac to develop the necessary physical displacement of the blood pumping sac 56 into its compressed condition. It will be apparent that the secure fastening of this ventricle is essential during the systole stage in view of the full pressure being asserted against the interior of the shell upon extension of the air sac 59.

Figure 8:
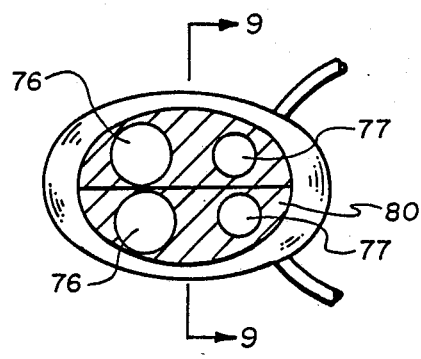
FIG. 8 illustrates another embodiment of the present invention wherein two ventricles are combined within a single construction and wherein the view corresponds to a cross section of the bridging structure and openings to the blood sac as illustrated in FIG. 3.
Figure 9:
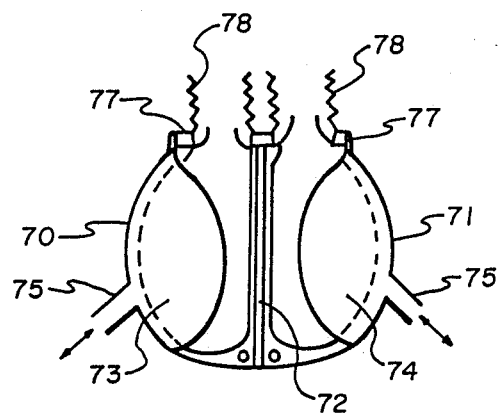
FIG. 9 is a graphic representation of the single construction artificial heart with a pair of enclosing shells coupled to a common separating wall.
Figure 10:
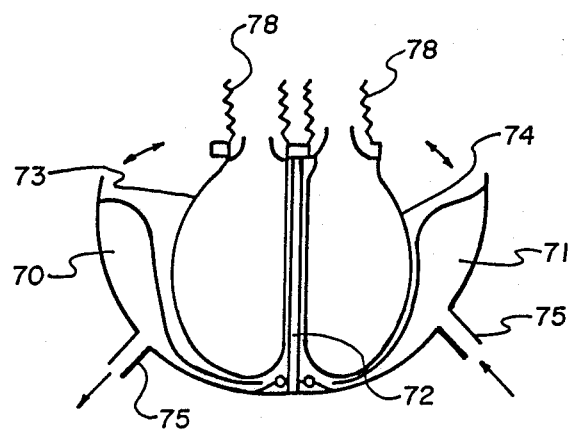
FIG. 10 illustrates separation of the shells to enable insertion or withdrawal of the respective ventricles comprising the artificial heart system.

FIGS. 8, 9 and 10 illustrate a further embodiment of the present invention wherein the shell of the left ventricle 70 and the shell of the right ventricle 71 can be combined to eliminate the dead space between the shells and the chest cavity. These shell components are joined at a common wall 72 which divide the shell into the respective left 73 and right 74 ventricle sections. The separating wall 72 can advantageously have an arcuate waveform cross-section (not shown in the figure) to allow a more physiologic location of the inflow and outflow ports 76 and 77 in FIG. 8. Separate drive lines 75 and 76 power the system to function as a normal heart. Inlet 76 and outlet 77 ports are constructed in accordance with the previous disclosure. FIG. 9 illustrates graph sections 78 which are attached to soft tissue at the pulmonary artery or aorta.

A stiff positioning ring 80 is formed as a single structure to maintain proper alignment of the respective openings and their attached graphs and atrial cuffs. This is in accordance with the description provided with respect to a single stiffening member identified in FIG. 3 as item 23. This stiffening member maintains the proper orientation of the respective one way valves with respect to the attached circulatory system openings.

The dual-ventricle device illustrated in FIGS. 8 and 9 is shown in an open configuration in FIG. 10. This construction enables attachment of both left and right ventricles as part of a single artificial heart, with subsequent emplacement of the dual-shell system with its respective drive line 75.

Other features of operation and construction will be apparent based on the foregoing description for the single ventricle. The total volume of this dual-shell heart is approximately 40 percent less because of the elimination of dead space between the ventricles. It also offers the advantage of less opportunity for growth of bacteria between the ventricles.

The general invention disclosed herein will greatly facilitate implantation of artificial hearts as a regular procedure in preserving the life of those patients waiting for heart transplants or for other patients for whom the artificial heart is a last resort. It will eliminate connectors between blood containing components and make the insertion of valves with or without valve rings possible. Because the ventricles can be rolled up, squeezed, bent and reduced in volume, they can be easily handled and surgically implanted. Any contained air can be easily removed and visually inspected by virtue of the transparent nature of the ventricle. Suture lines in the atrium, aorta and pulmonary arteries can readily be tested under pressure for leaks before putting the patient at risk.

It will be apparent to those skilled in the art that the embodiments disclosed herein are merely representative of the inventive concepts hereafter defined in the claims. Accordingly, no limitation is intended by way of disclosure except in accordance with proper construction of the following specific claims.

I claim:

1. An artificial ventricle for use as part of a total artificial heart for implantation within a living being as part of its circulatory system, said ventricle comprising:
   a soft and flexible blood pumping sac having extended (diastolic) and contracted (systolic) configurations and wall structure sufficient in size to develop adequate stroke volume for sustaining life within the living being, said blood sac having sufficient flexibility to collapse to a substantially flattened, squeezed or rolled up soft structure of reduced size to facilitate surgical implantation within restricted space of the chest cavity of the living being;
   an inlet port positioned within the wall structure and having means for attachment to the atrium or other soft tissue of the circulatory system to form a continuous flow line therewith, said inlet port including means for receiving a oneway valve;
   an outlet port positioned within the wall structure and having means for attachment to the aorta, pulmonary artery or other soft tissue of the circulatory system to form a continuous flow line therewith, said outlet port including means for receiving a one-way valve;
   a semi-rigid shell structurally separable from the blood pumping sac and having closure means for developing closed and open configurations respectively permitting insertion around and removal from the blood pumping sac in situ with the circulatory system;
   said closure means and shell providing a closed shell configuration slightly larger in shape and size at an interior surface than the extended configuration of the wall structure of the blood pumping sac and being structured to totally enclose the sac;
   said shell including an opening for the inlet and outlet ports and sealing means to provide a circumferential seal at respective junctures of the shell with the inlet and outlet ports;
   said closure means and shell further providing an open configuration enabling insertion of the contracted sac through a shell opening and removal of the shell from around the sac without affecting attachment of the sac as part of the circulatory system; and
   pump means coupled through the rigid shell to enable alternating extension and collapse of the blood pumping sac in recurring pumping manner when the shell is in the closed configuration to allow inflow and expulsion of blood from the blood sac.

2. An artificial ventricle as defined in claim 1, wherein the blood sac comprises a thin walled structure of silicone.

3. An artificial ventricle as defined in claim 1, wherein the inlet and outlet ports are of semi-rigid construction and are interconnected by a bridging structure which maintains the respective ports in relatively fixed positions during surgical implantation.

4. An artificial ventricle as defined in claim 3, wherein the semi-rigid construction of the ports and interconnecting bridge structure provides a sealing situs for operation of the sealing means with the shell.

5. An artificial ventricle as defined in claim 4, wherein the sealing means further comprises a skirt member integrally formed at one end of the shell corresponding to the position of the ports of the blood sac, said skirt including an opening which geometrically conforms to the exterior construction of the ports and interconnecting bridge structure at the sealing situs to provide a contact juncture which assists in sealing the interior of the shell with respect to the enclosed blood sac.

6. An artificial ventricle as defined in claim 1, wherein the blood sac is prepared by a vacuum forming process.

7. An artificial ventricle as defined in claim 1, wherein the blood sac is prepared by a solution casting process.

8. An artificial ventricle as defined in claim 6, wherein the blood sac is formed from a composition of thermo-setting elastomers.

9. An artificial ventricle as defined in claim 7, wherein the blood sac is formed from a composition of thermo-setting elastomers.

10. An artificial ventricle as defined in claim 7, wherein the blood sac is formed from a composition of silicone.

11. An artificial ventricle as defined in claim 1, wherein the pump means includes (i) a fluid drive sac formed integrally with an interior surface of the shell, said drive sac having flexible structure and sufficient volume for expansion within the shell in the closed configuration to develop the desired stroke volume for the ventricle, and (ii) a fluid drive line for delivering fluid to extend and contract the drive sac during pumping action.

12. An artificial ventricle as defined in claim 1, wherein the blood sac further includes a stiff positioning ring having two openings for receiving the respective one-way valves, said ring openings being operable to maintain the one-way valves in proper alignment with respect to attached soft tissue.

13. An artificial heart comprising a pair of artificial ventricles as defined in claim 1, wherein the respective blood sacs correspond to left and right ventricles of the artificial heart and the respective shells enclosing each ventricle are joined at a common wall which divides the artificial heart into left and right ventricle sections.

14. An artificial heart as defined in claim 13, further comprising a single positioning ring coupled to the respective blood sacs and having four openings for receiving the one-way valves associated with each respective ventricle to thereby maintain the valves in proper alignment with attached soft tissue of the circulatory system.

15. An artificial heart as defined in claim 13 in which the common wall between the ventricles has an arcuate waveform cross-section waveform which positions the respective ports in a preferred physiological position for attachment within the chest cavity.

16. An artificial ventricle for use as part of a total artificial heat for implantation within a living being as part of its circulatory system, said ventricle comprising:
   a soft and flexible blood pumping sac having extended (diastolic) and contracted (systolic) configurations and wall structure sufficient in size to develop adequate stroke volume for sustaining life within the living being, said blood sac having sufficient flexibility to collapse to a substantially flattened, squeezed or rolled up soft structure of reduced size to facilitate surgical implantation within restricted space of the chest cavity of the living being;
   an inlet port positioned within the wall structure and having means for attachment to the atrium or other soft tissue of the circulatory system to form a continuous flow line therewith, said inlet port including means for receiving a one-way valve;

an outlet port positioned within the wall structure and having means for attachment to the aorta, pulmonary artery or other soft tissue of the circulatory system to form a continuous flow line therewith, said outlet port including means for receiving a one-way valve;

a semi-rigid shell structurally separable from the blood pumping sac and having closure means for developing closed and open configurations respectively permitting insertion around and removal from the blood pumping sac in situ with the circulatory system;

said shell comprising two shell components which are configured to join at each shell periphery to form a closed configuration;

said closure means including a connecting hinge element disposed at one edge of the joining peripheries to form a clamshell configuration capable of opening to permit insertion of the blood sac and enclosing around the blood sac to form a confining shell structure to limit expansion and displacement of the blood sac in response to operation of a pumping means;

said closure means and shell providing a closed shell configuration slightly larger in shape and size at an interior surface than the extended configuration of the wall structure of the blood pumping sac and being structured to totally enclose the sac;

said shell including an opening for the inlet and outlet ports and sealing means to provide a circumferential seal at respective junctures of the shell with the inlet and outlet ports;

said closure means and shell further providing an open configuration enabling insertion of the contracted sac through a shell opening and removal of the shell from around the sac without affecting attachment of the sac as part of the circulatory system; and pumping means coupled through the rigid shell to enable alternating extension and collapse of the blood pumping sac in recurring pumping manner when the shell is in the closed configuration to allow inflow and expulsion of blood from the blood sac.

17. An artificial ventricle as defined in claim 16, wherein the connecting hinge element comprises a bridging section of shell wall structure integral with each of the shell components and forming a continuous shell wall therwith which flexes at the bridging section to provide hinge action to facilitate opening and closing the shell structure.

18. An artificial ventricle as defined in claim 16, wherein the periphery of the respective shell component includes a tongue and groove attachment structure to provide a tight seal when the shell components are positioned in the closed configuration.

19. An artificial ventricle as defined in claim 16, further comprising latch means coupled near the shell opening for secure fastening of the respective shell components in sealed configuration around the inlet and outlet ports.

* * * * *